(12) United States Patent
Asmus et al.

(10) Patent No.: US 9,278,155 B2
(45) Date of Patent: *Mar. 8, 2016

(54) ADHESIVE COMPOSITIONS, ARTICLES INCORPORATING SAME AND METHODS OF MANUFACTURE

(75) Inventors: Robert A. Asmus, Hudson, WI (US); Beatrice C. Etzold, Hudson, WI (US); Joy A. Packard, Somerset, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/456,811

(22) Filed: Jun. 5, 2003

(65) Prior Publication Data
US 2004/0247655 A1 Dec. 9, 2004

(51) Int. Cl.
| | |
|---|---|
| A61F 13/02 | (2006.01) |
| A61L 15/58 | (2006.01) |
| C09J 133/24 | (2006.01) |
| C08K 5/053 | (2006.01) |
| C08L 1/00 | (2006.01) |
| C08L 5/00 | (2006.01) |

(52) U.S. Cl.
CPC .............. A61L 15/58 (2013.01); C09J 133/24 (2013.01); *C08K 5/053* (2013.01); *C08L 1/00* (2013.01); *C08L 5/00* (2013.01)

(58) Field of Classification Search
None
See application file for complete search history.

(56) References Cited

U.S. PATENT DOCUMENTS

| | | | |
|---|---|---|---|
| 2,838,421 A | 6/1958 | Sohl | 117/122 |
| 2,921,006 A * | 1/1960 | Schmitz et al. | 522/142 |
| RE24,906 E | 12/1960 | Ulrich | |
| 3,389,827 A | 6/1968 | Abere et al. | |
| 3,645,835 A | 2/1972 | Hodgson | 161/146 |
| 3,865,770 A | 2/1975 | Blake | 260/27 R |
| 3,993,552 A | 11/1976 | Assarsson et al. | 204/159 |
| 4,112,213 A | 9/1978 | Waldman | |
| 4,273,135 A | 6/1981 | Larimore et al. | 128/640 |
| 4,299,231 A | 11/1981 | Karmann et al. | |
| 4,310,509 A | 1/1982 | Berglund et al. | 424/28 |
| 4,323,557 A | 4/1982 | Rosso et al. | |
| 4,366,814 A | 1/1983 | Riedel | |
| 4,413,080 A | 11/1983 | Blake | 524/187 |
| 4,472,480 A | 9/1984 | Olson | |
| 4,524,064 A | 6/1985 | Nambu | 424/81 |
| 4,539,996 A | 9/1985 | Engel | 128/640 |
| 4,551,490 A | 11/1985 | Doyle et al. | |
| 4,593,053 A * | 6/1986 | Jevne et al. | 523/111 |
| 4,595,001 A | 6/1986 | Potter et al. | 128/156 |
| 4,684,558 A | 8/1987 | Keusch et al. | 428/40 |
| 4,699,146 A | 10/1987 | Sieverding | 128/640 |
| 4,706,680 A | 11/1987 | Keusch et al. | 128/640 |
| 4,737,410 A | 4/1988 | Kantner | |
| 4,750,482 A | 6/1988 | Sieverding | 128/156 |
| 4,849,224 A | 7/1989 | Chang et al. | 424/434 |
| 4,855,294 A | 8/1989 | Patel et al. | 514/212 |
| 4,867,742 A | 9/1989 | Calderon | |
| 4,867,748 A | 9/1989 | Samuelsen | |
| 4,909,244 A | 3/1990 | Quarfoot et al. | |
| 4,931,282 A * | 6/1990 | Asmus et al. | 424/78.06 |
| 4,989,607 A | 2/1991 | Keusch et al. | 128/640 |
| 5,059,424 A | 10/1991 | Cartmell et al. | |
| 5,088,483 A | 2/1992 | Heinecke | |
| 5,106,629 A | 4/1992 | Cartmell et al. | |
| 5,133,821 A | 7/1992 | Jensen | |
| 5,160,315 A | 11/1992 | Heinecke et al. | |
| RE34,279 E | 6/1993 | Blake | 524/145 |
| 5,225,473 A | 7/1993 | Duan | 524/388 |
| 5,270,358 A * | 12/1993 | Asmus | 524/55 |
| 5,276,079 A * | 1/1994 | Duan et al. | 524/386 |
| 5,338,490 A * | 8/1994 | Dietz et al. | 252/500 |
| 5,354,790 A | 10/1994 | Keusch et al. | 523/300 |
| 5,362,497 A | 11/1994 | Yamada et al. | 424/449 |
| 5,369,155 A | 11/1994 | Asmus | 524/55 |
| 5,389,376 A * | 2/1995 | Duan et al. | 424/448 |
| 5,409,966 A * | 4/1995 | Duan et al. | 522/152 |
| 5,423,737 A | 6/1995 | Cartmell et al. | |
| 5,438,988 A * | 8/1995 | Duan et al. | 600/391 |
| 5,447,492 A | 9/1995 | Cartmell et al. | |
| 5,531,855 A | 7/1996 | Heinecke et al. | |
| 5,654,312 A | 8/1997 | Andrulis, Jr. et al. | 514/279 |
| 5,700,478 A | 12/1997 | Biegajski et al. | 424/434 |

(Continued)

FOREIGN PATENT DOCUMENTS

| | | |
|---|---|---|
| CN | 1306862 A | 8/2001 |
| CN | 1381975 | 11/2002 |

(Continued)

OTHER PUBLICATIONS

D. Bensky et al.; "Chinese Herbal Medicine—Materia Medica" (Revised Edition 1993).
Molyneaux "Water-Soluble Synthetic Polymers: Properties and Behavior" vol. 1, CRC Press, 1983; pp. 151-152.
Iscan, G. et al.; "Antimicrobial Screening of *Mentha piperita* Essential Oils"; Journal of Agricultural and Food Chemistry; 2002, 50, pp. 3943-3946.
International Search Report from related published PCT Application No. PCT/US2004/016676, dated Oct. 1, 2004; 3 pgs.
Written Opinion of the International Searching Authority from related PCT Application No. PCT/US2004/016676, dated Oct. 7, 2004; 5 pgs.

(Continued)

*Primary Examiner* — Hasan A Ahmed
(74) *Attorney, Agent, or Firm* — 3M Innovative Properties Company; Lynn R. Hunsberger

(57) ABSTRACT

A hydrophilic, pressure-sensitive adhesive composition comprising crosslinked poly(N-vinyl lactam), a swelling agent, and a modifying polymer in an amount sufficient to form a cohesive pressure-sensitive adhesive composition is provided. The composition is useful as a medical secural of percutaneous devices. The composition is also useful as a drug delivery device to deliver antimicrobial agents, pharmaceuticals or other active ingredients to or through skin. A method of preparation of the composition is also disclosed.

32 Claims, 1 Drawing Sheet

(56) References Cited

U.S. PATENT DOCUMENTS

| | | | |
|---|---|---|---|
| 5,704,905 A | 1/1998 | Jensen et al. | 602/58 |
| 5,714,225 A | 2/1998 | Hansen et al. | |
| 5,849,325 A | 12/1998 | Heinecke et al. | 424/443 |
| 5,976,117 A | 11/1999 | Dunshee et al. | 604/307 |
| 5,990,205 A | 11/1999 | Cordova | 524/55 |
| 6,004,969 A | 12/1999 | Hu | 514/282 |
| 6,149,614 A | 11/2000 | Dunshee et al. | 602/57 |
| 6,190,689 B1 | 2/2001 | Hoffmann et al. | |
| 6,210,699 B1 | 4/2001 | Acharya et al. | 424/435 |
| 6,264,976 B1 | 7/2001 | Heinecke et al. | 424/443 |
| 6,436,432 B2 | 8/2002 | Heinecke et al. | 424/443 |
| 6,458,341 B1 | 10/2002 | Rozzi et al. | 424/54 |
| 6,497,949 B1 | 12/2002 | Hyde et al. | 428/355 |
| 6,503,532 B1 | 1/2003 | Murty et al. | |
| 6,838,589 B2 | 1/2005 | Liedtke et al. | |
| 7,115,792 B2 | 10/2006 | Kartheus et al. | |
| 7,217,853 B2 | 5/2007 | Kulichikhin et al. | |
| 2002/0037977 A1 | 3/2002 | Feldstein et al. | 526/60 |
| 2002/0131994 A1 | 9/2002 | Schur et al. | 424/449 |
| 2003/0007999 A1 | 1/2003 | Blatchford et al. | 424/445 |
| 2004/0247654 A1* | 12/2004 | Asmus et al. | 424/449 |
| 2009/0187130 A1 | 7/2009 | Asmus et al. | |

FOREIGN PATENT DOCUMENTS

| | | |
|---|---|---|
| CN | 1387847 A | 1/2003 |
| DE | 44 16 927 C1 | 8/1995 |
| EP | 0 318 183 | 5/1989 |
| EP | 0 318 183 A2 | 5/1989 |
| EP | 0 506 300 A2 | 9/1992 |
| EP | 0 642 794 B1 | 3/1995 |
| EP | 0 750 905 A2 | 1/1997 |
| EP | 0 919 211 A2 | 6/1999 |
| GB | 2 115 431 A | 9/1983 |
| JP | 54-039385 | 3/1979 |
| JP | 57-042618 | 3/1982 |
| JP | 60-020976 | 2/1985 |
| JP | 1-166764 | 6/1989 |
| JP | 06-157327 | 6/1994 |
| JP | 7-501101 | 2/1995 |
| JP | 9-169633 | 6/1997 |
| JP | 10-045571 | 2/1998 |
| JP | 11-209269 | 8/1999 |
| JP | 2000-143484 | 5/2000 |
| JP | 2002-020257 | 1/2002 |
| JP | 2002-080386 | 3/2002 |
| JP | 2002-167335 | 6/2002 |
| JP | 2004-512314 | 4/2004 |
| WO | WO 89/07951 | 9/1989 |
| WO | 93/10201 | 5/1993 |
| WO | WO 93/10163 | 5/1993 |
| WO | WO 93/10201 | 5/1993 |
| WO | WO 00/16752 | 3/2000 |
| WO | WO 01/50994 A1 | 7/2001 |
| WO | WO 01/64229 A1 | 9/2001 |
| WO | 02/34304 | 5/2002 |
| WO | 03/080133 A1 | 10/2003 |
| WO | WO 2004/019920 A1 | 3/2004 |

OTHER PUBLICATIONS

International Preliminary Report on Patentability from the related PCT Application No. PCT/US2004/016676, dated Dec. 8, 2005; 6 pgs.

European Office Action from related Application No. 04753495.3-1214, dated May 20, 2009; 4 pgs.

Austrian Examination Report from related Singapore Application No. 200507789-6, dated Oct. 17, 2008; 3 pgs.

Austrian Written Opinion from related Singapore Application No. 200507789-6, dated Feb. 22, 2008; 3 pgs.

Austrian Written Opinion from related Singapore Application No. 200507789-6, dated 2007; 4 pgs.

Australian Office Action from related Application No. 2004245941, dated Mar. 20, 2009, 3 pgs.

Indian Office Action from related Application No. 3266/CHENP/2005, dated Feb. 20, 2008; 2 pgs.

Chinese Office action from related Application No. 200480019109.4, dated Dec. 7, 2007; 7 pgs.

Chinese Office action from related Application No. 200480019109.4, dated Aug. 1, 2008; 8 pgs.

Buhler, V, "Kollidon®", Chapter 3: Insoluble Kollidon grades (crospovidone, crospolyvidone), Aug. 1993, BASF; 2 pgs. (Exhibit A).

"PVP (Polyvinylprrolidone)," International Speciality Products, Brochure, Copyright © 2008, 13 pgs.

Japanese office action dated Aug. 31, 2010 from related JP Application No. 2006-514984; Including English Translation; 8 pgs.

"All You Need, All in One: Tegaderm CHG", 3M Health Care, St. Paul, MN. ©2011, 2014. Retrieved from the internet May 11, 2015: <URL:http://multimedia.3m.com/mws/media/501550O/tegaderm-chg-dressing-product-brochure.pdf>; 7 pages (copyright 2011/2014).

Karpanen, et al., "Antimicrobial activity of a chlorhexidine intravascular catheter site gel dressing", *J Antimicrob Chemother*, May 2011, 66:1777-1784.

Kohan, et al., "Experience with Two Different Chlorhexidine Gluconate Dressings for use on Central Venous Devices," poster presented at APIC (Association for Professionals in Infection Control), New Haven, Connecticut, Jun. 2013.

"New CDC Guidelines for Prevention of Intravascular Catheter-associated Infections Designate Chlorhexidine Gluconate-Impregnated Sponge as a Category 1B Recommendation Exclusively Based on Evidence Related to Biopatch© Protective Disk with CHG", Ethicon Inc., Somerville, New Jersey, Apr. 2011. Retrieved from the internet May 11, 2015: <URL:http://www.ethicon.com/news/newsinfo/corporate/20549>, 2 pages.

O'Grady, et al., "Guidelines for the Prevention of Intravascular Catheter-Related Infections, 2011", Department of Health and Human Services Center for Disease Control, 2011. Retrieved from the internet: <URL:http://www.cdc.gov/hicpac/pdf/guidelines/bsi-guidelines-2011.pdf>, 83 pages.

O'Grady, et al., "Summary of Recommendations: Guidelines for the Prevention of Intravascular Catheter-related Infections," *Clinical Infections Diseases*, May 2011; 52(9):1087-1099.

Pfaff, et al., "Use of a 1-Piece Chlorhexidine Glucomate Transparent Dressing on Critically Ill Patients", *Critical Care Nurse*, Aug. 2012, 32(4):35-40.

Timsit, et al., "Randomized Controlled Trial of Chlorhexidine Dressing and Highly Adhesive Dressing for Preventing Catheter-related Infections in Critically Ill Adults", *Am J Respir Crit Care Med*, Dec. 2012, 186(12):1272-1278.

World Health Organization, "Patient safety: Preventing bloodstream infections from central line venous catheters". Retrieved from the internet on May 8, 2015: <URL:http://www.who.int/patientsafety/implementation/bsi/en/>, 2 pages.

\* cited by examiner

ADHESIVE COMPOSITIONS, ARTICLES INCORPORATING SAME AND METHODS OF MANUFACTURE

FIELD OF THE INVENTION

This invention relates to adhesive compositions, articles made therewith and methods for producing adhesive compositions.

BACKGROUND OF THE INVENTION

Increasing the cohesiveness of certain hydrophilic adhesive compositions has often been accomplished by crosslinking the polymeric material in the composition. Depending on the polymer system, crosslinking of the polymer can have varying effects on both the cohesive and adhesive aspects of the adhesive composition. Pressure sensitive adhesives ("PSAs") are known in the art to possess properties including: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers and compositions containing polymers that exhibit the requisite viscoelastic properties resulting in a desired balance of tack, peel adhesion, and shear holding power.

Pressure sensitive adhesives may be produced using multifunctional crosslinkers or radiation induced crosslinking, and these adhesives can exemplify a range in adhesive and cohesive character. Where crosslinking agents are used, an optimal concentration of the crosslinking agent generally provides an increase in cohesiveness and adhesiveness. Increasing or decreasing the crosslinker beyond the optimal concentration for a given system can reduce both cohesiveness and adhesiveness in a manner as shown and described in U.S. Pat. No. 4,931,282. Consequently, the ability to tailor the adhesive and cohesive needs for a given application has been limited.

Hydrogels are one type of adhesive system where the adhesive and cohesive properties could be further optimized. In such systems, the crosslinking of the polymers has allowed for the inclusion of higher amounts of additives without reducing the cohesive properties of the composition below acceptable levels. However, the use of crosslinking agents in hydrogel systems are known to include residual components and undesired byproducts of the polymerization process. When crosslinking is induced by irradiation of the polymer, additives should be compatible with the irradiation process.

In the case of radiation induced crosslinking of poly vinyl lactam based adhesives, a minimum dose of radiation is necessary to achieve adequate cohesiveness. Significant reductions in adhesion however have required very high doses of radiation of solid poly (n-vinyl lactam). In turn, the higher doses of radiation result in compositions susceptible to cohesive failure.

Balanced against the need for improved cohesiveness, a continuing concern exists for biocompatibility in the preparation of hydrophilic polymers used as medical adhesives. Not only must the pressure-sensitive adhesive composition adhere to skin, but the adherence to living tissue should not cause skin irritation, toxicity reactions, or other deleterious effects.

A need exists to find a balance between the cohesive nature of certain medical adhesives compositions and the adhesive properties which facilitate bonding with living tissue. In compositions such as hydrogels, for example, it is desirable to increase the cohesive nature and absorptive swelling capacity of the adhesive compositions while maintaining a low modulus, conformability, and gentle-to-skin adhesiveness, and the ability to cleanly (e.g., without significant residue) remove the composition from skin and/or from a medical percutaneous device such as an IV catheter or the like. Additionally, adhesive compositions such as hydrogels should also retain their cohesive and adhesive properties in the presence of additives such as antimicrobial or therapeutic agents.

Any of a variety of percutaneous devices can present an infection risk to a patient. These devices include central venous access devices (CVADs), peripheral catheters, arterial catheters, orthopedic fixator and traction pins, wound drains and chest tubes, Kwires, pacemaker wires, tracheostomy tubes and various pressure monitors. For example, up to about ninety percent of all catheter-related sepsis occurs in patients with CVADs. It has been shown that most organisms invade the bloodstream through the catheter insertion site, either by migration along the catheters external surface or through contamination that enters the internal port of the device. The uses of CVADs although very beneficial, present a significant morbidity and mortality risk to patients in addition to significant financial costs for treatment of these related bacteremias. Consequently, a device that can significantly reduce these infection rates would be a significant advance in the art.

In addition to the aforementioned risk of infection from bacterial migration, movement of the catheter or "pistoning" of the catheter into the associated vein presents another a potential risk for facilitating the movement of bacteria and increasing the risk of infection as well as increasing the risk of trauma or irritation to the vein, known as phlebitis. This mechanical irritation increases the risk of both chemical irritation and infection.

An improved secural of the catheter can minimize the above problems as well as reduce the risk of infiltration, the inadvertent administration of infusate to the extravascular space or outside the vessel. Improved secural can also increase the life of the line so that less health care attention and manipulation is needed during the life of the line as well, which can also reduce the risk of infection.

SUMMARY OF THE INVENTION

In one aspect, the invention provides an adhesive composition comprising a first polymer comprising a cross-linked poly (N-vinyl lactam), a swelling agent, and a second modifying polymer swellable in the swelling agent. The first polymer forms a pressure sensitive adhesive in the presence of the swelling agent. Further, the second modifying polymer and the swelling agent reduce the adhesiveness of the first polymer while maintaining or improving the cohesion of the composition.

The composition of the invention may further comprise an antimicrobial agent. When present, the antimicrobial agent may be at a concentration up to 10% by weight. The poly (N-vinyl lactam) may be selected from N-vinyl-2-pyrrolidone, poly N-vinyl-2-valerolactam, poly N-vinyl-2-caprolactam, and combinations of the foregoing. The modifying polymer may comprise any of a variety of polymers that swell in the presence of the swelling agent, such as polysaccharide, polysaccharide derivatives, acrylate, acrylate derivatives, cellulose, cellulose derivatives, hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and dialyldimethyl ammonium chloride; and derivatives and combinations of the foregoing.

In other aspects, the swelling agent may comprise greater than 50% of the total weight of the composition. The first polymer may comprise between 5% and 45% by weight, and the second polymer may comprise between 0.1% and 40% by weight of the composition.

In still other aspects, the first polymer may be poly N-vinyl-2-pyrrolidone; the swelling agent may be triglycerol and the second polymer may be selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and dialyldimethyl ammonium chloride; and derivatives and combinations of the foregoing; and the antimicrobial agent is chlorhexidine gluconate.

In another aspect of the invention, the foregoing compositions may be configured as a medical sealant for sealing a junction between living skin and a medical instrument penetrating through the skin. In other aspects, the composition of the invention may be applied to a suitable backing and configured as a tape (e.g., a medical tape), a wound dressing, a bandage or a medical skin covering. Other configurations for the invention include a pharmaceutical delivery device comprising: an adhesive layer as described herein for contacting skin and a backing layer, with the adhesive layer adhered to the backing layer.

In still another aspect, the invention provides a method for the manufacture of an adhesive composition, which comprises irradiating with gamma radiation the precursor of the first polymer to cross-link the precursor, and mixing the crosslinked first polymer with the swelling agent and the second polymer to provide the composition.

These and other aspects of the invention will be more apparent to those skilled in the art upon consideration of the remainder of the disclosure, including the Detailed Description of the Invention and the appended claims.

DETAILED DESCRIPTION OF THE INVENTION

Figure 1:
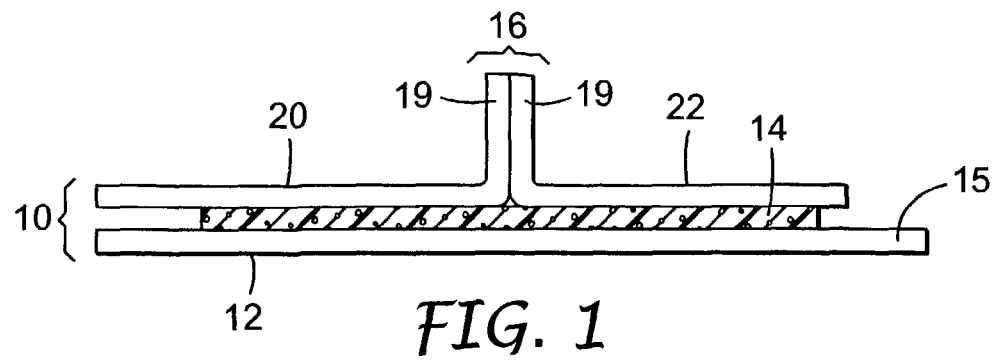
FIG. 1 is a side view of a medical sealant containing the adhesive composition of the present invention.

"Solid" means that poly(vinyl lactam) is not required to be mixed with any other material prior to irradiation to crosslink such poly(vinyl lactam). No mixing with solvents, swelling agents or chemical crosslinking agents is required to prepare radiation-crosslinked poly(vinyl lactam) useful for the present invention. Commercially available non-crosslinked poly(vinyl lactam) can be employed in particulate form for irradiation to crosslink such poly(vinyl lactam). "Essentially unirradiated" as applied to additives useful with, radiation-crosslinked poly(N-vinyl lactam) refers to the additive as not being subjected to irradiation during the crosslinking of the poly(N-vinyl lactam) and as not subjected to irradiation at any other time at a dosage which would degrade the additives.

"Swelling agent" is defined as a substance capable of swelling polymer.

"Modifying polymer" is defined as a polymer that, in the presence of the swelling agent, exhibits an observed reduction in the adhesiveness of the composition and maintains or increases its cohesiveness.

"Adhesion" or "adhesive" refers to a property of a substance rendering it capable of bonding other substances together, typically by surface attachment.

"Cohesion" refers to a property of a substance rendering it resistant to separation or by which it tends to stay together rather than separate or break apart.

This invention provides an adhesive composition formulated with a blend of a crosslinked poly (vinyl lactam), a swellable polymer and a swelling agent. The inventive composition can also contain a biologically active agent, such as an antimicrobial agent to suppress regrowth of resident skin microflora, for example.

In one application, the adhesive composition of the present invention may be used as a secural device like those used to secure central vascular lines that have been inserted into a human patient. The composition of the invention provides a cohesive gel-like system with adhesiveness to human skin while possessing desired cohesiveness.

The adhesive composition has adequate adhesion to skin during application, provides secural to the line to inhibit movement of the catheter to minimize pistoning of the catheter in the vein, and typically leaves no significant residue when removed.

The compositions of the invention are also useful as adhesive gels for the delivery of therapeutic agents onto or through the skin. Penetration enhancing agents or excipients could be added when a pharmaceutical or active agent for topical or transdermal delivery is desired. Additives to adjust the pH, buffer the pH, alter the ionic strength of the adhesive composition as well as pigments to alter the opacity, color, reflectivity or strength of the gel is also considered.

Poly (N-Vinyl) Lactam Polymer

The adhesive composition of the present invention comprises a swellable, crosslinked poly(N-vinyl lactam), a swelling agent and a modifying polymer present in an amount sufficient to form a cohesive, pressure- sensitive adhesive composition. The amount of swelling agent to be mixed with the crosslinked swellable poly(N-vinyl lactam) can range from about 50 to about 90 weight percent of the composition. Consequently, exclusive of any biocompatible and/or therapeutic and/or ionically-conductive materials to be added to the composition, the weight percent of the swellable poly(N-vinyl lactam) can be from about 5, and often about 10 to about 50 weight percent. When the poly(N-vinyl lactam) is poly(N-vinyl pyrrolidone), the weight percent of poly(N-vinyl pyrrolidone) can range from about 15 to about 45 percent. In particular embodiments, the poly(N-vinyl pyrrolidone) can range from about 18 percent to about 35 percent.

In most embodiments, the adhesive composition of the present invention comprises a swellable, poly(N-vinyl lactam) that is radiation-crosslinked, typically while the lactam is in a solid form. In other embodiments, the poly (N-vinyl lactam) is crosslinked by free-radical polymerization, either in bulk or in solution, of a precursor containing an N-vinyl lactam monomer, optionally other monomers, and a crosslinking compound as described in U.S. Pat. No. 4,931,282, which is incorporated herein by reference.

Poly(N-vinyl lactam) useful in the present invention can be provided in any form susceptible to being crosslinked such as the solid forms described in U.S. Pat. Nos. 4,931,282; 5,225,473; and 5,389,376, the disclosures of which are incorporated in their entirety herein by reference thereto. Nonlimiting examples of solid forms include particles, pellets, sheets, flakes, and bulk objects of various shapes, and coated objects of various shapes. Typically, the poly(N-vinyl lactam) is in the form of particles of a size less than about 1 cm in diameter, more typically from about 0.1 micron to 0.250 cm and often from about 10 microns to about 1000 microns. Alternatively, the poly (n-vinyl) lactam can be crosslinked in solution. Poly (N-vinyl lactam) can be a noncrosslinked homopolymer or a noncrosslinked copolymer containing N-vinyl lactam monomeric units, which after irradiation becomes swellable in a swelling agent and is biocompatible with mammalian (e.g., human) skin. In most embodiments, a noncrosslinked homopolymer or noncrosslinked copolymer of poly (N-vinyl) lactam may be used which is soluble in a biocompatible swelling agent. Nonlimiting examples of N-vinyl lactam monomers are N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. Typically, the poly(N-vinyl lactam) is a homopolymer of N-vinyl-2-pyrrolidone.

Nonlimiting examples of comonomers useful with the aforementioned N-vinyl lactam monomers include N,N-dimethylacrylamide, acrylic acid, methacrylic acid, hydroxyethylmethacrylate, acrylamide, 2-acrylamido-2-methyl-1-propane sulfonic acid or its salt, and vinyl acetate. Normally, N-vinyl lactam monomeric units will comprise no less than about 50 weight percent of the monomeric units present in the poly(N-vinyl lactam) in solid state form. Typically, N-vinyl lactam monomeric units comprise a majority of total monomeric units of the polymer, and more typically, the N-vinyl lactam monomeric units comprise 70 to 100 percent by weight of the poly(N-vinyl lactam) and often 90 to 100 percent by weight of the poly(N-vinyl lactam).

Noncrosslinked N-vinyl lactam homopolymer and N-vinyl pyrrolidone/vinyl acetate copolymers are commercially available. Nonlimiting sources of commercially available poly(N-vinyl pyrrolidone) useful for the present invention include Aldrich Chemical Co. of Milwaukee, Wis., BASF of Parsippany, N.J., ISP (GAF) of Wayne, N.J., Dan River Corporation of Danville, Va., and Spectrum Chemical Manufacturing Corporation of Gardena, Calif. Poly(N-vinyl lactam) can have a Fikentscher K-value of at least K-15, and normally at least K-60 more often K-90, or even K-120. Other Fikentscher K-values are possible. Fikentscher K-values are described in Molyneaux, Water-Soluble Polymers: Properties and Behavior, Vol. 1, CRC Press, 1983, pp. 151-152.

After exposure to ionizing radiation, poly(N-vinyl lactam) can have a Swelling Capacity in water of at least about 15, typically at least about 30, and often at least about 40 as described in U.S. Pat. No. 5,409,966, which is incorporated herein by reference.

Swellable Modifying Polymers

The modifying polymer is present in the adhesive composition to maintain and/or increase cohesiveness while reducing adhesiveness. When added with the swelling agent, the modifying polymer becomes solublized or suspended in the swelling agent. Typically, the modifying polymer will form a viscous solution or viscous gel when combined with the swelling agent in a ratio of modifying polymer to swelling agent of 1:9.

The choice of swelling agent typically will determine the appropriate modifying polymer to accomplish a reduction in adhesion while maintaining or improving cohesion of the adhesive composition. Modifying polymers that are poorly solubilized in one swelling agent may be highly swollen in a different swelling agent for use in the present invention. In some embodiments, examples of suitable modifying swellable polymers include, but are not limited to, polysaccharides, polysaccharide derivatives, acrylates, acrylate derivates, cellulose, cellulose derivatives, and combinations thereof.

In particular embodiments, modifying swellable polymers for use in the present invention are hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

The amount of modifying polymer can range up to about 50 weight percent of the composition. Consequently, exclusive of any biocompatible and/or therapeutic and/or ionically-conductive materials to be added to the composition, the weight percent of the modifying polymer can be from about 0.1 to about 40 weight percent. When the modifying polymer is hydroxypropyl guar, the weight percent of hydroxypropyl guar can range from about 1 to about 20 percent.

Swelling Agents

The compositions of the present invention contain a swelling agent which can swell both the crosslinked poly(N-vinyl lactam) polymer and the modifying polymer, and which is biocompatible with human skin. Nonlimiting examples of swelling agents useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol swelling agents which do not cause skin irritation or toxic reaction, and water.

Depending on the ultimate use desired for the adhesive composition, non-volatile and/or volatile swelling agents may be used. One suitable swelling agent may comprise volatile swelling agent and non-volatile swelling agent, such as a mixture of glycerin or polyethylene glycol with water. In some embodiments, non-volatile swelling agents may be used by themselves such as, for example, glycerin or polyethylene glycol. Likewise, volatile swelling agents such as water may be used by themselves in the compositions of the invention. For this invention, "essentially non-volatile" means that a swelling agent as used in the present invention will render the adhesive polymer, such as radiated poly(N-vinyl lactam), sufficiently cohesive and pressure sensitive adhesive, such that less than ten percent (10%) of a given volume of swelling agent evaporates after exposure to processing or storage conditions.

The swelling agent can be added in an amount ranging from about 50 to about 90 weight percent of the adhesive composition and preferably from about 60 to about 80 weight percent. In some embodiments, glycerin and polyethylene glycol are chosen to be the essentially non-volatile swelling agent. Both glycerin and polyethylene glycol can comprise up to 100 weight percent of the swelling agent.

Other non-limiting examples of swelling agents which would be useful include monohydric alcohols, (e.g. ethanol, isopropanol, n-propanol), polyhydric alcohols (propylene glycol, dipropylene glycol, polyethylene glycol (PEG-2 to PEG-45M, preferably of molecular weight between 200 and 600) glycerol, polyglycerols (e.g. diglycerin, triglycerol, polyglycerin-3, hexaglycerol and decaglycerol), sorbitol and polyhydric alcohol ethoxylates (e.g. sorbeth-6, sorbeth-30, glycereth-1 to glycereth-31) methoxides of polyethylene glycol (Methoxy PEG-2 to Methoxy PEG 100), methoxides of polyhydric alcohol ethoxylates (e.g. glycereth-7 methoxide).

The swelling agent is typically a liquid. In some embodiments, humectant—type solid swelling agents like sorbitol could be used in conjunction with a co-swelling agent in order to dissolve and remain as a liquid. Other humectants that could also be employed as swelling agents or co-swelling agents include: 1,2,6-hexanetriol, acetamide mea, aluminum hydroxide, arginine pca, butoxypropanol, butylene glycol, dimethyl imidazolidinone, dimethylsilanol hyaluronate, dipotassium glycyrrhizate, erythritol, ethoxydiglycol, fructose, glutamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pca, lactamide mea, lactic acid, lactitol, lactose, lysine pca, magnesium pca, maltitol, manganese pca, mannitol, mel (honey extract), menthyl pca, methyl gluceth-10, methyl gluceth-20, pca (pidolic acid), lactamide, polydextrose, polyglucuronic acid, polyglyceryl sorbitol, potassium pca, ppg-20 methyl glucose ether, ppg-38-buteth-37, saccharide isomerate, serica, silk amino acids, sodium carboxymethyl chitin, sodium lactate, sodium mannuronate methylsilanol, sodium pca, sodium pca methylsilanol, sodium polyglutamate, soluble collagen, sorbitol, sucrose, tea-lactate, tea-pca, trehalose, trilactin, urea, xylitol, *zea mays*, zinc pca, and combinations thereof.

Antimicrobial Agents

The adhesive composition of the present invention can deliver an antimicrobial agent to the skin in and around the percutaneous device, reducing the likeliness of an infection to the device or to treat infections of the skin or wounds. In most embodiments, the antimicrobial agent is added in levels up to 10% by weight of the total composition.

There are numerous biologically active materials, which include antimicrobial agents. Examples of antimicrobial agents include Parachlorometaxylenol; triclosan; Chlorhexidine and its salts such as Chlorhexidine Gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymixin B).

The following active ingredients could also be used to suppress the regrowth or possibly treat an infection of microorganisms in the present invention: 2,2-thiobis(4-chlorophenol); 4,4-isopropylidenediphenol; 5-amino-6-chloro-o-cresol; acetaminosalol; alcloxa; aldioxa; aluminum acetate; aluminum benzoate; aluminum diacetate; aluminum formate; aluminum phenolsulfonate; ammonium iodide; ammonium phenolsulfonate; benzisothiazolinone; benzotriazole; benzoxiquine; benzylparaben; berberine chloride; boric acid; cetethyl morpholinium ethosulfate; cetethyldimonium bromide; cetrimonium tosylate; cetylpyridinium chloride; chloramine-t; chlorothymol; cloflucarban; cocotrimonium chloride; colloidal sulfur; copper usnate; dedm hydantoin; dedm hydantoin dilaurate; dequalinium acetate; dequalinium chloride; dibromopropamidine diisethionate; dichloro-m-xylenol; dichlorophene; dichlorophenyl imidazoldioxolan; diiodomethyltolylsulfone; dimethyl hydroxymethylpyrazole; dimethylaminostyryl heptyl methyl thiazolium iodide; dodecylbenzyltrimonium chloride; domiphen bromide; ferulic acid; fluorosalan; glyoxal; hydroxymethyl dioxoazabicyclooctane; hydroxypropyl bistrimonium diiodide; ichthammol; isodecylparaben; isopropyl sorbate; lapyrium chloride; laurtrimonium trichlorophenoxide; lauryl isoquinolinium bromide; lauryl isoquinolinium saccharinate; laurylpyridinium chloride; m-cresol; mandelic acid; MDM hydantoin; MEAa-iodine; melaleuca alternifolia; methylbenzethonium chloride; mixed cresols; nonoxynol-12 iodine; nonoxynol-9 iodine; o-cresol; oxyquinoline benzoate; oxyquinoline sulfate; p-chlorophenol; p-cresol; PEG-15 dedm hydantoin; PEG-15 dedm hydantoin stearate; PEG-5 dedm hydantoin; PEG-5 dedm hydantoin oleate; phenol; phenoxyethylparaben; phenyl salicylate; polymethoxy bicyclic oxazolidine; potassium iodide; potassium lactate; potassium phenoxide; potassium troclosene; quaternium-14; quaternium-24; quaternium-8; ricinoleamidopropyltrimonium methosulfate; sodium iodide; sodium p-chloro-m-cresol; sodium phenolsulfonate; sodium phenoxide; sodium usnate; steapyrium chloride; strontium peroxide; tea-sorbate; tetrabutyl ammonium bromide; thiabendazole; triacetin; undecylenamide dea; undecylenamide mea; undecylenamidopropyltrimonium methosulfate; undecyleneth-6; undecylenoyl peg-5 paraben; usnic acid; zinc acetate; zinc borate; zinc phenolsulfonate; zinc sulfate; zinc undecylenate; and combinations of the foregoing.

The following actives could also be of use to also reduce regrowth of microorganisms on skin: 2-bromo-2-nitropropane-1,3-diol; 4-hydroxybenzoic acid; 5-bromo-5-nitro-1,3-dioxane; 7-ethylbicyclooxazolidine; ammonium benzoate; ammonium bisulfite; ammonium propionate; ammonium sulfite; behentrimonium chloride; benzalkonium bromide; benzalkonium chloride; benzalkonium saccharinate; benzethonium chloride; benzoic acid; benzyl alcohol; benzylhemiformal; bromochlorophene; butyl benzoate; butylparaben; calcium benzoate; calcium paraben; calcium propionate; calcium salicylate; calcium sorbate; calcium undecylenate; cetalkonium chloride; cetearalkonium bromide; cetrimonium bromide; cetrimonium chloride; chloroacetamide; chlorobutanol; chlorophene; chloroxylenol; chlorphenesin; climbazole; dehydroacetic acid; diazolidinyl urea; dibromohexamidine isethionate; dichlorobenzyl alcohol; dimethyl oxazolidine; DMDM hydantoin; ethyl benzoate; ethylparaben; formaldehyde; formic acid; glutaral; hexamidine; hexamidine diisethionate; hexamidine paraben; hexetidine; hydrogenated tallowtrimonium chloride; imidazolidinyl urea; iodopropynyl butylcarbamate; isobutyl benzoate; isobutylparaben; isopropyl benzoate; isopropyl cresols; isopropylparaben; lauralkonium bromide; lauralkonium chloride; laurtrimonium bromide; laurtrimonium chloride; magnesium benzoate; magnesium propionate; magnesium salicylate; MEA o-phenylphenate; MEA-benzoate; MEA-salicylate; MEA-undecylenate; methenamine; methyl benzoate; methylchloroisothiazolinone; methyldibromo glutaronitrile; methylisothiazolinone; methylparaben; myristalkonium chloride; myristalkonium saccharinate; myrtrimonium bromide; o-cymen-5-ol; o-phenylphenol; olealkonium chloride; p-chloro-m-cresol; phenoxyethanol; phenoxyisopropanol; phenyl benzoate; phenyl mercuric acetate; phenyl mercuric benzoate; phenyl mercuric borate; phenyl mercuric bromide; phenyl mercuric chloride; phenylparaben; piroctone olamine; polyaminopropyl biguanide; potassium benzoate; potassium butylparaben; potassium ethylparaben; potassium metabisulfite; potassium methylparaben; potassium o-phenylphenate; potassium paraben; potassium propionate; potassium propylparaben; potassium salicylate; potassium sorbate; potassium sulfite; propionic acid; propyl benzoate; propylparaben; quaternium-15; salicylic acid; sodium benzoate; sodium bisulfite; sodium butylparaben; sodium dehydroacetate; sodium ethylparaben; sodium formate; sodium hydroxymethylglycinate; sodium iodate; sodium metabisulfite; sodium methylparaben; sodium o-phenylphenate; sodium paraben; sodium propionate; sodium propylparaben; sodium salicylate; sodium sorbate; sodium sulfite; sodium undecylenate; sorbic acid; soytrimonium chloride; stearalkonium chloride; steartrimonium chloride; tallowalkonium chloride; tallowtrimonium chloride; thimerosal; triclocarban; triclosan; undecylenic acid; zinc pyrithione; and combinations of the foregoing.

Biocompatible and/or Therapeutic and/or Ionically-Conductive Additives

Depending upon the use of the hydrophilic, pressure-sensitive adhesive composition of the present invention, various other biocompatible and/or therapeutic and/or ionically-conductive materials can be included in the composition.

Hydrophilic, pressure-sensitive adhesive compositions of the present invention can also be used in the delivery of pharmaceuticals to or through human skin, such as topical or transdermal drug delivery systems. The pharmaceutical or other active ingredient can be compounded with the adhesive composition after poly(N-vinyl lactam) has been radiation-crosslinked, minimizing any possible deleterious interaction of the pharmaceutical or active ingredient with ionizing radiation in dosages sufficient to crosslink poly(N-vinyl lactam).

The hydrophilic, pressure-sensitive adhesive composition can also be used in therapeutic skin coverings, such as dressings, wound closure materials, tapes, and the like. Preferably, for skin covering uses, other biologically active materials can be added to the composition of the present invention after irradiation of poly(N-vinyl lactam) without deleteriously affecting the biologically active material. Nonlimiting examples of such other biologically active materials include broad spectrum antimicrobial agents such as those disclosed in U.S. Pat. No. 4,310,509, which disclosure is incorporated by reference, where it is desired to reduce bacteria levels to minimize infection risk or treat the effects of infections at the skin or skin openings of a patient.

When the adhesive compositions are used as an electrically conductive component of biomedical electrodes, the adhesive composition can also optionally include water to improve ionic conductivity in levels varying from 20% to 100%. Ionically-conductive electrolytes can also be added to the composition without deleteriously affecting the electrolyte or the resulting composition. Nonlimiting examples of electrolytes include ionic salts dissolved in the composition, such as lithium chloride, lithium perchlorate, sodium citrate, and potassium chloride.

A type of therapeutic procedure both involving application of electrical current to skin of a patient and a pharmaceutical is iontophoresis, which delivers an iontophoretically active pharmaceutical to or through human skin with aid of an electrical current.

Other therapeutic agents can be added, such as herbal medicines. Herbal medicines capable of use in the present invention are shown and described in co-pending, co-assigned patent application entitled "Hydrophilic Adhesive Compositions for Delivery of Herbal Medicines," U.S. Ser. No. 10/456,810, filed the same day herewith.

Other biocompatible and/or therapeutic materials can be added to the composition such as compounds to buffer the pH of the composition to provide a non-irritating pH for use with sensitive mammalian skin tissue or to otherwise maximize antimicrobial activity. Also, penetration enhancing agents or excipients can be added to the composition when the pharmaceutical or other active agent for topical or transdermal delivery so requires.

Irradiation Crosslinking of Poly(N-Vinyl Lactam)

Poly(N-vinyl lactam) in any solid form may be crosslinked for use in the invention when subjected to ionizing radiation from a high-energy source. Nonlimiting examples of ionizing radiation include alpha, beta, gamma, electron-beam, and x-ray radiation. Of these sources of ionizing radiation, electron-beam irradiation and gamma irradiation are most typical. Sources of electron-beam radiation are commercially available, including an Energy Sciences Inc. Model CB-150 Electrocurtain Electron Beam Processor. Sources of gamma irradiation are commercially available from Atomic Energy of Canada, Inc. using a cobalt-60 high-energy source.

Ionizing radiation dosages are measured in megarads (mRad) or kilograys (kGy). Doses of ionizing radiation can be administered in a single dose of the desired level of ionizing radiation or in multiple doses which accumulate to the desired level of ionizing radiation. The dosage of ionizing radiation cumulatively can range from about 25 kGys to about 400 kGys and preferably from about 25 kGys to about 200 kGys. Preferably, ionizing radiation can achieve the desired level of crosslinking of poly(N-vinyl lactam) when the cumulative dosage of ionizing radiation exceeds 100 kGys (10 mRads).

Poly(N-vinyl lactam) can be irradiated in a solid form with ionizing radiation in a package or container where the temperature, atmosphere, and other reaction parameters can be controlled. One method of irradiating the poly (N-vinyl lactam) in the present invention is described in U.S. Pat. No. 5,409,966, which is incorporated herein by reference. Depending upon the control of the irradiation conditions, poly(N-vinyl lactam) can be irradiated in a batch or continuous process.

Method of Preparing Hydrophilic Adhesive Compositions

A method of preparing a pressure-sensitive adhesive composition of the present invention comprises mixing crosslinked poly(N-vinyl lactam) with a swelling agent and a modifying polymer, and other additives in a solvent which is may be somewhat volatile at or above ambient temperatures. Typically, the swelling agent, modifying polymer, and other additives, such as antimicrobial agents, are in essentially unirradiated form. Examples of suitable volatile solvents include water, ethanol, methanol, and isopropanol. A quantity of the resulting suspension is then cast onto a surface of a substrate, such as a release liner or a backing material and then stored. The volatile solvent is evaporated by heating such as by the application of microwave energy, infrared energy, or by convective air flow or the like, in order to form a cohesive, pressure-sensitive adhesive composition on the substrate. Often, a drying oven heated to about 65° C. may be employed for the evaporation step. A product release liner can optionally be laminated over the exposed surface of the composition to protect it from contamination.

In some embodiments, coating of the adhesive composition can be applied to the surface of a substrate. Suitable wet coating thicknesses may range from about 0.125 mm to about 1.25 mm so that, after evaporation of solvent, a dry coating thickness is obtained within the range from about 0.05 mm to about 0.38. Such coatings can be applied to any of a variety of substrate surfaces to act as an adhesive layer for the substrate and providing an adhesive composition with a low profile.

The method of preparing the compositions of the invention can be a batch process or a continuous line process. If prepared by a continuous process, the laminate of a liner, field of cohesive, pressure-sensitive adhesive composition, and substrate can be wound on roll for bulk packaging and further processing or can be cut using dies known to those skilled in the art into individual units.

Medical Sealant

The adhesive composition of the present invention provides a medical sealant for medical applications requiring reduced adhesion while maintaining or improving cohesiveness to allow clean removal from a substrate. In one embodiment, the medical sealant is used for IV catheters or CVADs.

FIG. 1 shows a sectional view of a medical sealant 10 having a first release liner 12, a layer 14 of pressure sensitive adhesive composition of the present invention coated on first release liner 12, and protected until use second release liner 16. Typically, first release liner 12 has a first release value that has lower than the release value of second release liner 16. First release liner 12 also optionally contains a section 15 that extends beyond the perimeter of second release liner 16 to facilitate application of medical sealant 10 during application.

Second release liner 16 is composed of two parts, 20 and 22. Parts 20 and 22 each end in a tab 19 proximate the center of medical sealant 10. Tabs 19 can extend perpendicular from layer 14 and is not attached to layer 14. Each of tabs 19 can be differential lengths to one another to improve grasping.

Figure 2A:
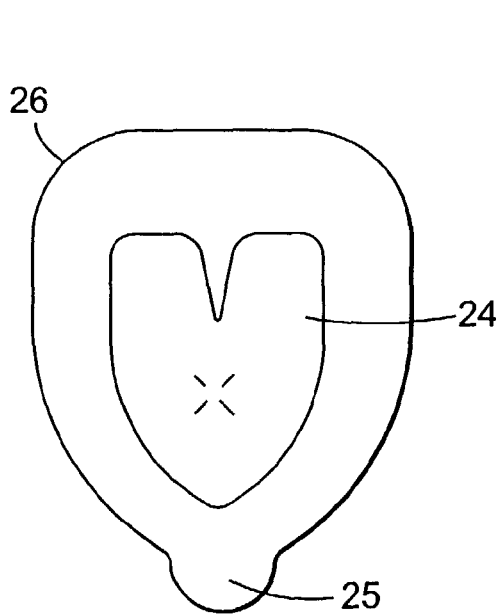
FIG. 2a is a bottom plan view of a medical sealant containing the adhesive composition of the present invention.
Figure 2B:
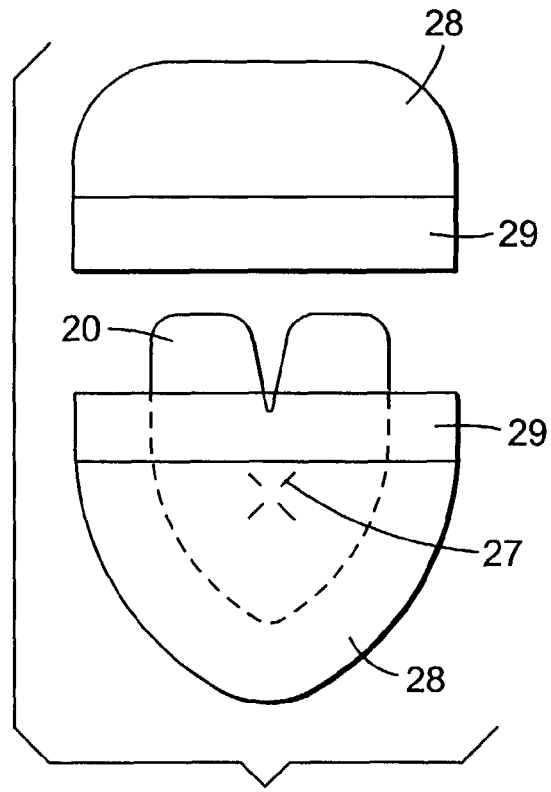
FIG. 2b is a top plan view of a medical sealant containing the adhesive composition of the present invention.

FIGS. 2a and 2b show a bottom and top plan view of the medical sealant using the adhesive composition of the present invention. For use, first release liner 26 shown in FIG. 2a is removed by grasping extend section 25 and the layer 24 of pressure-sensitive adhesive composition can be applied to the skin of the patient. After application to the patient, the tabs 29 of second release liner 28 are grasped and gently pulled in opposite directions towards the perimeter of medical sealant 20. Second release liner 28 optionally contains demarcation 27 indicating an optimal location for medical sealant 20 to be placed over the catheter insertion site to add in placement on a patient's skin.

FIG. 2a show adhesive composition 24 in a generally heart-shaped configuration. This configuration aids in placement of adhesive composition 24 containing antimicrobial agents to optimize secural of the lumen and hub of a catheter. The tops of the heart-shaped configuration split to go over the hub when used with catheter insertion. Most embodiments employ a heart-shaped configuration for the above reasons, however other shapes are possible with the present invention.

Figure 3:
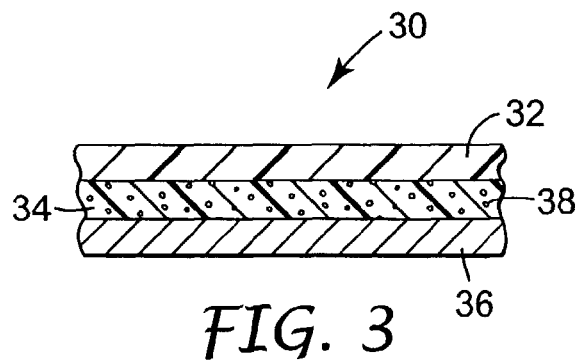
FIG. 3 is a sectional view of a medical sealant containing the adhesive composition of the present invention.

As shown in FIG. 3, medical sealant 30 contains antimicrobial agent 38 in layer 34 by adding agent 38 to essentially unirradiated swelling agent or composition prior to coating on first release liner 36 and second release liner 32. Alternatively, layer 34 can be used as a caulkable sealant according to U.S. Pat. No. 4,931,282 (Asmus et al.), the disclosure of which is incorporated by reference herein. Optionally other layers can be present between layer 32 and layer 34 to house pharmaceuticals or other therapeutic agents.

The adhesive layer 14 can be coated on the first and second release liners 12 and 16 by a variety of processes, including, direct coating, lamination, and hot lamination. Non-limiting examples of such release liners commercially available include siliconized polyethylene terephthalate films commercially available from H. P. Smith Co. and fluoropolymer coated polyester films commercially available from 3M under the brand "ScotchPak™" release liners.

The methods of lamination and hot lamination involve the application of pressure, or heat and pressure, respectively, on the layer of adhesive layer 14 to the first release liner 12. The temperature for hot lamination ranges from about 50° C. to about 250° C., and the pressures applied to both lamination and hot lamination range from 0.1 $Kg/cm^2$ to about 50 $Kg/cm^2$.

The adhesive of the present invention can also optionally be used in other applications, for example, as a part of a medical tape, a wound dressing, a bandage of general medicinal utility, or other medical device having water moisture absorbing properties. The adhesive layer may be coated on a layer of backing material selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel™ 4056" and "Hytrel™ 3548" branded polyester elastomers available from E.I. DuPont de Nemours and Company of Wilmington, Del., "Estane" branded polyurethanes available from B.F. Goodrich of Cleveland, Ohio or "Q-thane" branded polyurethanes available from K.J. Quinn & Co. of Malden, Mass. Other non-limiting examples of such backing materials are polyethylene, ethylene-vinyl acetate copolymer, polyethylene-aluminum-polyethylene composites, and "ScotchPak™" brand backings commercially available from Minnesota Mining and Manufacturing Company of St. Paul, Minn. (3M).

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

The therapeutic agent useful in the present invention can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

Biomedical Electrodes

Biomedical electrodes employing hydrophilic, pressure-sensitive adhesive compositions of the present invention having electrolyte contained therein are useful for diagnostic and therapeutic purposes. In its most basic form, a biomedical electrode comprises a conductive medium contacting mammalian skin and a means for electrical communication interacting between the conductive medium and electrical diagnostic, therapeutic, or electrosurgical equipment. One embodiment of a biomedical electrode for use with the adhesive compositions of the present invention are described in U.S. Pat. No. 5,409,966, which is incorporated herein by reference.

A further description of the invention may be found in the following examples.

EXAMPLES

GLOSSARY of COMPONENTS

| Trade Name | Chemical Name | Manufacturer, Address |
|---|---|---|
| Ganex V-216 | Polyvinylpyrrolidone/Hexadecane copolymer | ISP, Wayne, NJ |
| Mirapol A-15 | Polyquaternium-2 | Rhodia, Cranbury, NJ |
| Merquat 2200 | Polyquaternium-7 | Calgon, Pittsburgh, PA |
| UCARE JR-125 | Polyquaternium-10 | Amerchol, Danbury, CT |
| Quatrisoft LM-200 | Polyquaternium-24 | Amerchol |
| UCARE LK | Polyquaternium-10 | Amerchol |
| 0.64% EBVP | Crosslinked PVP with 0.64% Ethylene - bis-N-vinyl-2-pyrrolidone (EBVP) crosslinker | 3M/St Paul, MN |
| 1.28% EBVP | Crosslinked PVP with 1.28% EBVP crosslinker | 3M |
| Jaguar HP-120 | Hydroxypropyl Guar (HPG) | Rhodia, Cranbury, NJ |
| Celquat L-200 | Polyquaternium-4 | National Starch & Chemical/Bridgewater, NJ |
| Celquat SC-230M | Polyquaternium-10 | National Starch & Chemical |
| Celquat SC-240C | Polyquaternium-10 | National Starch & Chemical |
| Jaguar HP-60 | Hydroxypropyl Guar | Rhodia |
| Natrosol type 250HR CS | Hydroxyethyl cellulose | Aqualon |
| Natrosol Plus type 330 CS | Cetyl hydroxyethylcellulose | Aqualon |
| Cellosize HEC QP-52,000-H | Hydroxyethyl cellulose | Dow Chemical |
| UCARE JR-30M | Polyquaternium-10 | Amerchol |
| UCARE LR-30M | Polyquaternium-10 | Amerchol |
| EHEC XXHIGH 0100 | Ethylhydroxy ethyl cellulose | Aqualon |
| Polyox WSR-301 | Polyethylene oxide | Amerchol |
| Ganex P904 LC | Butylated poly vinyl pyrrolidone | ISP |
| Tego SO 6 | Sorbeth-6 | Degussa |
| CHG Solution B.P. | 20% Chlorhexidine Gluconate in Water | Xttrium Labs |
| XPVP | Gamma crosslinked K-90D polyvinylpyrrolidone | ISP Plasdone K-90D PVP processed with 15 Mrad gamma radiation |
| Diglycerol | Diglycerol | Solvay Interox, Houston, Texas |
| Polyglycerol-3 | Triglycerol | Solvay Interox, Houston, Texas |

Examples 1-67

Compositions were prepared by mixing the liquid components together and then quickly pouring in the dry powdered polymers and vigorously hand stirring for approx 30 seconds. The material is placed between two release liners and pressed to 1 mm thickness with a press. The formulas were evaluated for reducing the adhesiveness of the crosslinked polyvinylpyrrolidone gel without losing cohesive strength resulting in adhesive residue. The gel compositions were applied to clean human forearms and allowed to remain for approximately 3-5 minutes before removing. Adhesion was judged high (H) if on removing it stretched the skin, medium (M) if it was considered adhesive but less than high, low (L) if it took little force to peel it from the skin and the skin was not moved as the gel was removed. Residue was rated '0' if no residue was left, very slight (VSL) if a detectable amount of residue was discernable by touch, slight (SL) if the residue was visible and high (H) if a significant amount was left on the skin.

TABLE 1

Compositions and Results of Adhesion and Adhesive Residue Tests for Examples 1-67

| Ex. No. | XPVP Amount (wt. %) | Sorbeth-6 Amount (wt. %) | Second Polymer Type | Amt. (wt. %) | CHG Amount (wt. %) | Water Amount (wt. %) | Adhesion (H, M, L) | Residue (0, VSL, SL, H) |
|---|---|---|---|---|---|---|---|---|
| 1 | 30.0 | 57.0 | Ganex V-216 | 2.0 | 2.0 | 9.0 | H | 0 |
| 2 | 28.0 | 57.0 | Ganex V-216 | 4.0 | 2.0 | 9.0 | M-H | 0 |
| 3 | 26.0 | 57.0 | Ganex V-216 | 6.0 | 2.0 | 9.0 | M | VSL |
| 4 | 24.0 | 57.0 | Ganex V-216 | 8.0 | 2.0 | 9.0 | M | VSL |
| 5 | 30.0 | 57.0 | Mirapol A-15 | 2.0 | 2.0 | 9.8 | L-M | 0 |
| 6 | 28.0 | 57.0 | Mirapol A-15 | 4.0 | 2.0 | 10.5 | L-M | VVSL |
| 7 | 26.0 | 57.0 | Mirapol A-15 | 6.0 | 2.0 | 11.3 | M | SL |
| 8 | 24.0 | 57.0 | Mirapol A-15 | 8.0 | 2.0 | 12.0 | VL | SL |
| 9 | 16.0 | 57.0 | Merquat 2200 | 16.0 | 2.0 | 9.0 | H | VSL |
| 10 | 13.0 | 63.0 | Merquat 2200 | 13.0 | 2.0 | 9.0 | H | VSL |
| 11 | 10.0 | 69.0 | Merquat 2200 | 10.0 | 2.0 | 9.0 | H | H |
| 12 | 16.0 | 57.0 | UCARE JR-125 | 16.0 | 2.0 | 9.0 | L-M | 0 |
| 13 | 13.0 | 63.0 | UCARE JR-125 | 13.0 | 2.0 | 9.0 | M | 0 |
| 14 | 10.0 | 69.0 | UCARE JR-125 | 10.0 | 2.0 | 9.0 | M | VSL |
| 15 | 16.0 | 57.0 | UCARE LK | 16.0 | 2.0 | 9.0 | L | 0 |
| 16 | 13.0 | 63.0 | UCARE LK | 13.0 | 2.0 | 9.0 | L | 0 |
| 17 | 10.0 | 69.0 | UCARE LK | 10.0 | 2.0 | 9.0 | M | 0 |
| 18 | 16.0 | 57.0 | Quatrisoft LM-200 | 16.0 | 2.0 | 9.0 | L | 0 |
| 19 | 13.0 | 63.0 | Quatrisoft LM-200 | 13.0 | 2.0 | 9.0 | L | VSL |
| 20 | 10.0 | 69.0 | Quatrisoft LM-200 | 10.0 | 2.0 | 9.0 | L | VSL |
| 21 | 16.0 | 57.0 | 0.64% EBVP | 16.0 | 2.0 | 9.0 | M | 0 |
| 22 | 13.0 | 63.0 | 0.64% EBVP | 13.0 | 2.0 | 9.0. | H | VSL |
| 23 | 10.0 | 69.0 | 0.64% EBVP | 10.0 | 2.0 | 9.0 | H | SL |

TABLE 1-continued

Compositions and Results of Adhesion and Adhesive Residue Tests for Examples 1-67

| Ex. No. | XPVP Amount (wt. %) | Sorbeth-6 Amount (wt. %) | Second Polymer Type | Amt. (wt. %) | CHG Amount (wt. %) | Water Amount (wt. %) | Adhesion (H, M, L) | Residue (0, VSL, SL, H) |
|---|---|---|---|---|---|---|---|---|
| 24 | 16.0 | 57.0 | 1.28% EBVP | 16.0 | 2.0 | 9.0 | M | VSL |
| 25 | 13.0 | 63.0 | 1.28% EBVP | 13.0 | 2.0 | 9.0 | H | H |
| 26 | 10.0 | 69.0 | 1.28% EBVP | 10.0 | 2.0 | 9.0 | H | H |
| 27 | 16.0 | 57.0 | Salcare SC 96 | 16.0 | 2.0 | 9.0 | VH | 0 |
| 28 | 13.0 | 63.0 | Salcare SC 96 | 13.0 | 2.0 | 9.0 | VH | VSL |
| 29 | 13.0 | 63.0 | Polyhydroxy ethyl methacrylate | 13.0 | 2.0 | 9.0 | H | SL |
| 30 | 16.0 | 57.0 | UCARE JR-30M | 16.0 | 2.0 | 9.0 | L-M | 0 |
| 31 | 13.0 | 63.0 | UCARE JR-30M | 13.0 | 2.0 | 9.0 | M | 0 |
| 32 | 10.0 | 69.0 | UCARE JR-30M | 10.0 | 2.0 | 9.0 | M-H | 0 |
| 33 | 16.0 | 57.0 | UCARE LR-30M | 16.0 | 2.0 | 9.0 | L | 0 |
| 34 | 13.0 | 63.0 | UCARE LR-30M | 13.0 | 2.0 | 9.0 | L | 0 |
| 35 | 10.0 | 69.0 | UCARE LR-30M | 10.0 | 2.0 | 9.0 | L | 0 |
| 36 | 16.0 | 57.0 | EHEC XX HIGH 0100 | 16.0 | 2.0 | 9.0 | H-VH | 0 |
| 37 | 16.0 | 57.0 | Polyox WSR-301 | 16.0 | 2.0 | 9.0 | H | 0 |
| 38 | 13.0 | 63.0 | Polyox WSR-301 | 13.0 | 2.0 | 9.0 | M-H | SL |
| 39 | 10.0 | 69.0 | Polyox WSR-301 | 10.0 | 2.0 | 9.0 | H | SL |
| 40 | 16.0 | 57.0 | Jaguar HP-120 | 16.0 | 2.0 | 9.0 | L | 0 |
| 41 | 13.0 | 63.0 | Jaguar HP-120 | 13.0 | 2.0 | 9.0 | L | 0 |
| 42 | 10.0 | 69.0 | Jaguar HP-120 | 10.0 | 2.0 | 9.0 | L-M | 0 |
| 43 | 16.0 | 57.0 | Celquat L-200 | 16.0 | 2.0 | 9.0 | L-M | 0 |
| 44 | 13.0 | 63.0 | Celquat L-200 | 13.0 | 2.0 | 9.0 | M-H | 0 |
| 45 | 10.0 | 69.0 | Celquat L-200 | 10.0 | 2.0 | 9.0 | M-H | VSL |
| 46 | 16.0 | 57.0 | Celquat SC230M | 16.0 | 2.0 | 9.0 | L | 0 |
| 47 | 13.0 | 63.0 | Celquat SC230M | 13.0 | 2.0 | 9.0 | L-M | 0 |
| 48 | 10.0 | 69.0 | Celquat SC230M | 10.0 | 2.0 | 9.0 | M | 0 |
| 49 | 16.0 | 57.0 | Celquat SC240C | 16.0 | 2.0 | 9.0 | L | 0 |
| 50 | 13.0 | 63.0 | Celquat SC240C | 13.0 | 2.0 | 9.0 | L-M | 0 |
| 51 | 10.0 | 69.0 | Celquat SC240C | 10.0 | 2.0 | 9.0 | M | 0 |
| 52 | 16.0 | 57.0 | Jaguar HP60 | 16.0 | 2.0 | 9.0 | L | 0 |
| 53 | 13.0 | 63.0 | Jaguar HP60 | 13.0 | 2.0 | 9.0 | L | 0 |
| 54 | 10.0 | 69.0 | Jaguar HP60 | 10.0 | 2.0 | 9.0 | L-M | 0 |
| 55 | 30.0 | 57.0 | Ganex P904 LC | 2.0 | 2.0 | 9.0 | VH | 0 |
| 56 | 28.0 | 57.0 | Ganex P904 LC | 4.0 | 2.0 | 9.0 | VH | 0 |
| 57 | 26.0 | 57.0 | Ganex P904 LC | 6.0 | 2.0 | 9.0 | H-VH | 0 |
| 58 | 24.0 | 57.0 | Ganex P904 LC | 8.0 | 2.0 | 9.0 | H-VH | VSL |
| 59 | 16.0 | 57.0 | Natrosol type 250 HHR CS | 16.0 | 2.0 | 9.0 | L-M | 0 |
| 60 | 13.0 | 63.0 | Natrosol type 250 HHR CS | 13.0 | 2.0 | 9.0 | L-M | 0 |
| 61 | 10.0 | 69.0 | Natrosol type 250 HHR CS | 10.0 | 2.0 | 9.0 | M | VSL |
| 62 | 16.0 | 57.0 | Natrosol Plus type 330 CS | 16.0 | 2.0 | 9.0 | L | 0 |
| 63 | 13.0 | 63.0 | Natrosol Plus type 330 CS | 13.0 | 2.0 | 9.0 | L | 0 |
| 64 | 10.0 | 69.0 | Natrosol Plus type 330 CS | 10.0 | 2.0 | 9.0 | M | 0 |
| 65 | 16.0 | 57.0 | Cellosize HEC QP52000H | 16.0 | 2.0 | 9.0 | L | 0 |
| 66 | 13.0 | 63.0 | Cellosize HEC QP52000H | 13.0 | 2.0 | 9.0 | L-M | 0 |
| 67 | 10.0 | 69.0 | Cellosize HEC QP52000H | 10.0 | 2.0 | 9.0 | L-M | 0 |

Low (L) to Medium (M) adhesion rating to skin and no (0) adhesive residue was the preferred performance. When adhesive residue equals 0, the cohesive strength is high. The preferred Examples from Table 1 were: Examples 5, 12, 13, 15, 18, 21, 30-35, 40-44, 46-54, 59, 60, and 62-67.

Examples 68-73

Compositions were prepared using diglycerol and triglycerol as the primary swelling agents. Compositions were prepared by mixing the liquid components together and then quickly pouring in the dry powdered polymers and vigorously hand stirring for approx 30 seconds. The material is placed between two release liners and pressed to 1 mm thickness with a press. The components and amounts given in Table 2a.

TABLE 2a

Composition of Examples 68-73

| Example Number | XPVP Amount (wt. %) | Swelling agent Type | Amount (wt. %) | Jaguar HP-120 Amount (wt. %) | CHG Amount (wt. %) | Water Amount (wt. %) |
|---|---|---|---|---|---|---|
| 68 | 25.0 | Diglycerol | 61.0 | 3 | 2.0 | 9.0 |
| 69 | 24.0 | Diglycerol | 61.0 | 4 | 2.0 | 9.0 |
| 70 | 23.0 | Diglycerol | 61.0 | 5 | 2.0 | 9.0 |
| 71 | 22.0 | Diglycerol | 61.0 | 6 | 2.0 | 9.0 |
| 72 | 27.0 | triglycerol | 61.0 | 1 | 2.0 | 9.0 |
| 73 | 24.0 | triglycerol | 61.0 | 4 | 2.0 | 9.0 |

The compositions of Examples 68-73 were evaluated for adhesion to skin. The compositions were calendared between silicon release liners to an approximate thickness of 1 mm. These gel adhesive examples were then laminated on one side to a 2-mil (0.0508 mm) paper scrim. The paper scrim was used to eliminate stretching during the peel removal of gel adhesive. The laminated gel adhesives were cut to 1 inch (2.54 cm) by 2 inches (5.08 cm) samples. Skin adhesion testing was by placing the samples on the back of a human subject. The panelist was prepared by clipping the hair on the panelist's back and prepping with 70:30 isopropyl alcohol: water. Each sample was positioned so that the long axis of a sample was oriented perpendicular to the panelist's spine. Each sample was rolled down with one forward and one reverse pass using a 2 kg roller. A rotational randomization scheme was used to counter the effects of skin variations across the back. Samples were removed from the panelist's back using Pull-Peel Tester. Adhesion to the skin was measured as the peel force required to remove a sample at 180° angle at a 15 cm/min rate of removal. Adhesion was measured 30 minutes after initial application ($T_{30m}$), 1 day after application ($T_{1d}$), and 4 days after application ($T_{4d}$). For samples left on for 1 and 4 days, each sample was covered with a TEGADERM™ dressing (commercially available from 3M) to prevent lifting of the sample. Legging and Residue were also recorded in the study. Legging was rated on a scale for 1-3 with '1' meaning light legging, '2' meaning moderate legging, and '3' meaning heavy legging. Residue was rated as described for Examples 1-67. Results of 12 panelists were averaged.

TABLE 2b

Peel Adhesion on Skin and Legging of Examples 68-73

| Example Number | Peel Adhesion gm/2.54 cm | | | Legging (1, 2, 3) | | |
|---|---|---|---|---|---|---|
| | $T_{30m}$ | $T_{1d}$ | $T_{4d}$ | $T_{30m}$ | $T_{1d}$ | $T_{4d}$ |
| 68 | 51.6 | 30.5 | 21.4 | 0.08 | 0.08 | 0.00 |
| 69 | 54.0 | 22.4 | 22.7 | 0.08 | 0.00 | 0.00 |
| 70 | 33.5 | 22.0 | 18.2 | 0.08 | 0.00 | 0.00 |
| 71 | 27.4 | 29.7 | 25.8 | 0.00 | 0.08 | 0.13 |
| 72 | 108.4 | 89.0 | 58.0 | 0.67 | 1.88 | 1.18 |
| 73 | 46.6 | 61.8 | 33.2 | 0.17 | 0.79 | 0.39 |

Adding HPG to the composition reduced adhesion and legging, indicating increased cohesive strength. No adhesive residue was observed for the compositions of Examples 68-73. The preferred formulation was Example 73 due to the relatively flat adhesive profile over time.

What is claimed is:

1. An adhesive composition comprising: a first polymer comprising a crosslinked poly N-vinyl-2-pyrrolidone present in the composition in an amount of 5% to 35% by weight, wherein the crosslinked poly N-vinyl-2-pyrrolidone has a Swelling Capacity of at least 15 milliliters of water per gram of the crosslinked poly N-vinyl-2-pyrrolidone;
an essentially nonvolatile swelling agent present in an amount of 50% to 90% by weight, wherein the swelling agent is selected from the group consisting of polyhydric alcohols; glycerol; polyglycerols; polyhydric alcohol ethoxylates; and combinations of the foregoing;
a second modifying polymer swellable and/or soluble in the swelling agent, and present in an amount of 1% to 20% by weight, wherein the second modifying polymer is selected from the group consisting of hydroxypropyl guar; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; Polyquartenium-2; Polyquaternium-24; cetyl hydroxyethyl cellulose; and combinations of the foregoing; and
chlorhexidine gluconate in an amount up to 10% by weight of the total composition;
wherein the swelling agent, second modifying polymer, and antimicrobial agent are in essentially unirradiated form;
wherein the first polymer forms a pressure sensitive adhesive in the presence of the swelling agent; and
wherein the second modifying polymer, swelling agent, and first polymer demonstrate reduced adhesiveness relative to the pressure sensitive adhesive containing the first polymer and swelling agent, while at least maintaining the cohesion of the pressure sensitive adhesive containing the first polymer and swelling agent.

2. The composition of claim 1 wherein the swelling agent is selected from the group consisting of polyglycerols; polyhydric alcohol ethoxylates; and combinations of the foregoing.

3. The composition of claim 2 wherein the polyglycerols consist of diglycerin, triglycerol, polyglycerin-3, hexaglycerol, decaglycerol and combinations of the foregoing.

4. The composition of claim 1 wherein first polymer is poly N-vinyl-2-pyrrolidone; the swelling agent is triglycerol; the second modifying polymer is selected from the group consisting of hydroxypropyl guar, hydroxyethyl cellulose, hydroxypropyl cellulose, hydroxypropyl methylcellulose, polymeric quaternary ammonium salt of hydroxyethyl cellulose reacted with trialkyl ammonium substituted epoxide, copolymers of hydroxyethyl cellulose and diallyldimethyl ammonium chloride, and combinations of the foregoing; and the antimicrobial agent is chlorhexidine gluconate.

5. The composition of claim 1 configured as a medical sealant for sealing a junction between living skin and a medical instrument penetrating through the skin.

6. The composition of claim 5 wherein the medical sealant comprises first and second major surfaces, each major surface associated with a release liner.

7. The composition of claim 6 wherein a first release liner is associated with the first major surface and having a first release value, a second release liner is associated with the second major surface and having a second release value different from the first release value.

8. The composition of claim 7, wherein the adhesive composition is configured in a substantially heart-shaped outline.

9. A method for the manufacture of the adhesive composition of claim 1, the method comprising:
(a) irradiating with gamma radiation a precursor of the first polymer to cross-link the precursor; and
(b) mixing the crosslinked first polymer with the swelling agent, the second modifying polymer, and the antimicrobial agent to provide the composition of claim 1.

10. A medical article comprising a backing layer and the adhesive composition of claim 1.

11. The medical article according to claim 10, wherein the article comprises a medical tape, a wound dressing, a bandage or a medical skin covering.

12. A pharmaceutical delivery device comprising: an adhesive layer for contacting skin and a backing layer, the adhesive layer adhered to the backing layer and comprising the adhesive composition of claim 1.

13. The pharmaceutical delivery device according to claim 12, wherein the adhesive layer further comprises a topical, transdermal, or iontophoretic therapeutic agent.

14. The pharmaceutical delivery device according to claim 12, wherein the adhesive layer further comprises an excipient, a solvent, or a penetration enhancing agent.

15. The composition according to claim 1, wherein the amount of the swelling agent ranges from about 60 to about 80 weight percent of the composition.

16. The composition according to claim 1, wherein the poly N-vinyl-2-pyrrolidone is radiation-crosslinked.

17. The composition according to claim 1, wherein the crosslinked poly N-vinyl-2-pyrrolidone is radiation-crosslinked while in solid form.

18. The composition of claim 1 further comprising water.

19. An adhesive composition comprising:
a first polymer comprising a crosslinked poly N-vinyl-2-pyrrolidone present in the composition in an amount of 5% to 35% by weight, wherein the crosslinked poly N-vinyl-2-pyrrolidone has a Swelling Capacity of at least 15 milliliters of water per gram of the crosslinked poly N-vinyl-2-pyrrolidone;
an essentially nonvolatile swelling agent present in an amount of 50% to 80% by weight, wherein the swelling agent is selected from the group consisting of polyglycerols; polyhydric alcohol ethoxylates; and combinations of the foregoing;
a second modifying polymer swellable and/or soluble in the swelling agent, and present in an amount of 1% to 20% by weight, wherein the second modifying polymer is selected from the group consisting of hydroxypropyl guar; hydroxyethyl cellulose; polymeric quaternary ammonium salt of hydroxyethyl cellulose reacted with trialkyl ammonium substituted epoxide; copolymers of hydroxyethyl cellulose and diallyldimethyl ammonium chloride; Polyquaternium-2; Polyquaternium-24; cetyl hydroxyethyl cellulose; and combinations of the foregoing; and
chlorhexidine gluconate in an amount of up to 10% by weight of the total composition;
wherein the swelling agent, second modifying polymer, and antimicrobial agent are in essentially unirradiated form;
wherein the first polymer forms a pressure sensitive adhesive in the presence of the swelling agent; and
wherein the second modifying polymer, swelling agent, and first polymer demonstrate reduced adhesiveness relative to the pressure sensitive adhesive containing the first polymer and swelling agent, while at least maintaining the cohesion of the pressure sensitive adhesive containing the first polymer and swelling agent.

20. The composition of claim 19 configured as a medical sealant for sealing a junction between living skin and a medical instrument penetrating through the skin.

21. The composition of claim 19 further comprising water.

22. A medical article comprising a backing layer and the adhesive composition of claim 19 in contact with skin.

23. A medical article comprising a backing layer and an adhesive gel composition comprising:
a first polymer comprising a crosslinked poly N-vinyl-2-pyrrolidone present in the composition in an amount of 5% to 35% by weight, wherein the crosslinked poly N-vinyl-2-pyrrolidone has a Swelling Capacity of at least 15 milliliters of water per gram of the crosslinked N-vinyl-2-pyrrolidone
an essentially nonvolatile swelling agent present in an amount of 50% to 80% by weight, wherein the swelling agent is selected from the group consisting of polyhydric alcohols; glycerol; polyglycerols; polyhydric alcohol ethoxylates; and combinations of the foregoing;
a second modifying polymer swellable and/or soluble in the swelling agent, and present in an amount of 1% to 20% by weight, wherein the second modifying polymer is selected from the group consisting of hydroxypropyl guar; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; Polyquaternium-2; Polyquatenium-24; cetyl hydroxyethyl cellulose; and combinations of the foregoing; and
chlorhexidine gluconate in an amount of up to 10% by weight of the total composition;
wherein the swelling agent, second modifying polymer, and antimicrobial agent are in essentially unirradiated form;
wherein the first polymer forms a pressure sensitive adhesive in the presence of the swelling agent; and
wherein the second modifying polymer, swelling agent, and first polymer demonstrate reduced adhesiveness relative to the pressure sensitive adhesive containing the first polymer and swelling agent, while at least maintaining the cohesion of the pressure sensitive adhesive containing the first polymer and swelling agent.

24. The medical article of claim 23, wherein the adhesive gel composition further comprises water.

25. The medical article of claim 23, wherein the adhesive gel composition is configured as a medical sealant for sealing a junction between living skin and a medical instrument penetrating through the skin.

26. The medical article of 25, wherein the adhesive gel composition is in contact with skin.

27. The medical article of 23, wherein the adhesive gel composition is in contact with skin.

28. The medical article of claim 10, wherein the adhesive composition is in contact with skin.

29. An adhesive composition comprising:
- a first polymer comprising crosslinked poly N-vinyl-2-pyrrolidone particles present in the composition in an amount of 5% to 35% by weight, wherein the crosslinked poly N-vinyl-2-pyrrolidone particles are of a size less than 1cm;
- an essentially nonvolatile swelling agent present in an amount of 50% to 90% by weight, wherein the swelling agent is selected from the group consisting of polyhydric alcohols; glycerol; polyglycerols; polyhydric alcohol ethoxylates; and combinations of the foregoing;
- a second modifying polymer swellable and/or soluble in the swelling agent, and present in an amount of 1% to 20% by weight, wherein the second modifying polymer is hydroxypropyl guar; and
- chlorhexidine gluconate in an amount of up to 10% by weight of the total composition;
- wherein the first polymer forms a pressure sensitive adhesive in the presence of the swelling agent; and
- wherein the second modifying polymer, swelling agent, and first polymer demonstrate reduced adhesiveness relative to the pressure sensitive adhesive containing the first polymer and swelling agent, while at least maintaining the cohesion of the pressure sensitive adhesive containing the first polymer and swelling agent.

30. A medical article comprising a backing layer and the adhesive composition of claim 29.

31. The adhesive composition of claim 29 prepared by a method comprising:
- providing poly N-vinyl-2-pyrrolidone particles of a size less than 1cm;
- irradiating the poly N-vinyl-2-pyrrolidone particles to crosslink the particles; and
- mixing the crosslinked poly N-vinyl-2-pyrrolidone particles with the swelling agent, the second modifying polymer, and the antimicrobial agent to provide the composition of claim 29.

32. The composition of claim 31 wherein irradiating comprises applying ionizing radiation at a cumulative dosage of 25 kGys to 400 kGys.

* * * * *